US006720151B2

(12) United States Patent
Soll et al.

(10) Patent No.: US 6,720,151 B2
(45) Date of Patent: Apr. 13, 2004

(54) THERAPEUTIC AGENTS THAT INHIBIT THE TUP1 PATHWAY

(75) Inventors: David R. Soll, Iowa City, IA (US); Shawn R. Lockhart, Iowa City, IA (US); Rui Zhao, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/237,967

(22) Filed: Sep. 10, 2002

(65) Prior Publication Data

US 2003/0073154 A1 Apr. 17, 2003

Related U.S. Application Data

(60) Provisional application No. 60/317,980, filed on Sep. 10, 2001.

(51) Int. Cl.[7] .................................................. C12Q 1/68

(52) U.S. Cl. .................... 435/6; 435/254.22; 435/255.4

(58) Field of Search ............................... 435/6, 254.22, 435/255.4

(56) References Cited

U.S. PATENT DOCUMENTS 6,433,137 B1 * 8/2002 Johnson et al.
2002/0142468 A1 10/2002 Sundstrom

OTHER PUBLICATIONS

International Search Report for PCT/US02/25973 dated Feb. 20, 2003.
Balan, Inga et al., "The Candida albicans CDR3 Gene Codes for an Opaque–Phase ABC Transporter," Journal of Bacteriology, Dec. 1997, pp. 7210–7218, vol. 179, No. 23.
Bedell, Glenn et al., "Effects of Low Concentrations of Zinc on the Growth and Dimorphism of Candida albicans: Evidence for Zinc–Resistant and –Sensitive Pathways for Mycelium Formation," Infection and Immunity, Oct. 1979, pp. 348–354, vol. 26, No. 1., United States.
Braun, B. et al., "TUP1, CPH1 and EFG1 Make Independent Contributions to Filamentation in Candida albicans," The Genetics Society of America, May 2000, pp. 57–67, 155, United States.
Bruan, B. et al., "Identification and Characterization of TUP1–Regulated Genes in Candida albicans," The Genetics Society of America, Sep. 2000, pp. 31–44, 156, United States.
Care, R.S. et al., "The MET3 promoter: a new tool for Candida albicans molecular genetics," Molecular Microbiology, 1999, pp. 792–798, vol. 34(4), Blackwell Science Ltd.
Colombo, A. et al., "High Rate of non–albicans Candidemia in Brazilian Tertiary Care Hospitals," Diagn Microbiol Infect Dis, 1999, pp. 281–286, vol. 34, Elsevier Science, Inc., United States.

Hellstein, J. et al., "Genetic Similarity and Phenotypic Diversity of Commensal and Pathogenic Strains of Candida albicans isolated from the Oral Cavity," Journal of Clinical Microbiology, Dec. 1993, pp. 3190–3199, vol. 31, No. 12, American Society of Microbiology, United States.
Hube, B., et al., "Expression of seven members of the gene family encoding secretory aspartyl proteinases in Candida albicans," Molecular Microbiology, 1994, pp. 87–99, vol. 14(1).
Jabet, C. et al., "Characterization of the N–terminal Domain of the Yeast Transcriptional Repressor Tup1," The Journal of Biological Chemistry, Mar. 24, 2000, pp. 9011–9018, vol. 275, No. 12, American Society for Biochemistry and Molecular Biology., Inc., United States.
Kvaal, C. et al., "Misexpression fo the Opaque–Phase–Specific Gene PEP1 (SAP1) in the White Phase of Candida albicans Confers Increased Virulence in a Mouse Model of Cutaneous Infection," Infection and Immunity, Dec. 1999, pp. 6652–6662, vol. 67, No. 12, American Society for Microbiology, United States.
Lipshutz, R. et al. "High density synthetic oligonucleotide arrays," Nature Genetics Supplement, Jan. 1999, pp. 20–24, vol. 21, Nature America Inc., United States.
Morrow, B. et al., "Transcription of the Gene for a Pepsinogen, PEP1, is Regulated by White–Opaque Switching in Candida albicans," Molecular and Cellular Biology, Jul. 1992, pp. 2997–3005, vol. 12, No. 7.
Morrow, B., et al. "Coordinate Regulation of Two Opaque–Phase–Specific Genes during White–Opaque Switching in Candida albicans," Infection and Immunity, May 1993, pp. 1823–1828, vol. 61, No. 5, American Society for Microbiology, United States.
Odds, F.C., "Switch of Phenotype as an escape mechanism of the Intruder," Mycoses, 1997, pp. 9–12, vol. 40, Supplement 2, United States.
Pacheco–Rios, A. et al., "Mortality Associated with Systematic Candidlasis in Children," Archives of Medical Research, 1997, pp. 229–232, vol. 28, No. 2, Instituto Mexicano de Seguro Social, Mexico.
Pfaller, M., "Nosocomial Candidiasis: Emerging Species, Reservoirs, and Modes of Transmission," Clinical Infectious Diseases, May 1996, pp. 589–594, vol. 22, Supplement 2, University of Chicago Press, United States.

(List continued on next page.)

Primary Examiner—James Ketter
(74) Attorney, Agent, or Firm—Foley & Lardner

(57) ABSTRACT

A gene previously identified in the context of controlling filamentous growth in C. albicans, TUP1, plays a central role in the regulation of phenotype switching in Candida cells. Accordingly, compounds and therapeutic protocols can be screened for an ability to disrupt the pathway, controlled by TUP1, that is comprised of genes the expression of which affect switching specifically. Agents thus identified are candidates for use in treating or preventing candidiasis.

2 Claims, 1 Drawing Sheet

OTHER PUBLICATIONS

Soll, D. et al., "High–Frequency Switching in Candida Strains Isolated from Vaginitis Patients," *Journal of Clinical Microbiology*, Sep. 1987, pp. 1611–1622, vol. 25, No. 9, American Society for Microbiology, United States.

Soll, D. et al., "Multiple Candida Strains in the Course of a Single Systemic Infection," *Journal of Clinical Microbiology*, Aug. 1988, pp. 1448–1459, vol. 26, No. 8, American Society for Microbiology, United States.

Soll, D., "High–Frequency Switching in Candida albicans," *Clinical Microbiology Reviews*, Apr. 1992, pp. 183–203, vol. 5, No. 2., American Society for Microbiology, United States.

Soll, D., "The Emerging Molecular Biology of Switching in Candida albicans," *ASM News*, Aug. 1996, pp. 415–420, vol. 62, No. 8, American Society for Microbiology, United States.

Srikantha, T. et al., "The Sea Pansy Renilla reniformis Luciferase Serves as a Sensitive Bioluminescent Reporter for Differential Gene Expression in Candida albicans," *Journal of Bacteriology*, Jan. 1996, pp. 121–129, vol. 178, No. 1, American Society for Microbiology, United States.

* cited by examiner

THERAPEUTIC AGENTS THAT INHIBIT THE TUP1 PATHWAY

This invention was made in part with government support awarded by the U.S. National Institutes of Health under Grant No. 2RO1 AI39735-06. The United States government has certain rights in this invention.

BACKGROUND OF THE INVENTION

The present invention relates generally to an approach for developing pharmaceuticals and treatment protocols that are effective against Candida-associated pathologies.

Fungal diseases have become a major medical problem and are growing in severity, given the rising incidence of immunosuppression associated with AIDS, diabetes, cancer therapies, and organ transplantation, among other conditions. Debilitated patients thus affected are especially susceptible to fungal pathogens, most of which are opportunists.

The yeast Candida can exist both as a non-virulent colonizer (commensal) and as a pathogen. Candidiasis is increasingly widespread, with hospitalized and immunocompromised patients at greatest risk, and has become the sixth most common form of pathogenic infection. Systemic Candida infections may be lethal, with a mortality rate of 50% in adults and up to 65% in infants. Reviewed in Pfaller (1996); see also Colombo et al. (1999). The risk of death from systemic infection most strongly correlates with the time between the first detected infection and the onset of anti-fungal treatment. Pacheco-Rios et al. (1997).

The pathogenic success of Candida depends in part upon phenotypic plasticity. The most prominent Candida pathogen, *C. albicans*, exhibits a bud-hypha phenotype transition that occurs en masse, in response to various stimuli, and provides *C. albicans* with the capacity to penetrate tissue and to disseminate. Odds (1997). *Candida albicans* also undergoes spontaneous, reversible, high frequency switching of phenotypes, which does not occur en masse.

More specifically, *C. albicans* may switch reversibly between a phenotype characterized by white colonies and a phenotype characterized by opaque colonies. Soll (1992). This white/opaque switching occurs at higher frequencies in isolates from deep versus superficial mycoses, Jones et al. (1994), at higher frequencies in infecting versus commensal isolates from the oral cavity, Hellstein et al. (1993), within sites of infection, Soll et al. (1987), (1988), and within sites of commensalism, Soll (1992). Switching also has been shown to regulate virulence in animal models. Kvaal et al. (1999).

High-frequency phenotypic switching in *C. albicans* involves the coordinated regulation of a battery of phase-specific genes. The gene products of several of these genes facilitate pathogenesis, Soll (1992) and Soll (1996). These products include secreted aspartyl proteinases, Hube et al. (1994), Morrow et al. (1992), (1993) and White et al. (1993), and drug resistance proteins, Balan et al. (1997).

Switching provides a mechanism for enhancing pathogenesis via generation of phenotypic plasticity. Thus, switching results in antigenic variability on the yeast cell surface. No single phenotypic trait has been found to be responsible for Candida pathogenesis, however. Moreover, uncertainty has surrounded the extent of overlap in respective regulatory circuitry for the switching event (white⇌opaque) and the dimorphism event (hypha⇌budding cell), as well as the significance of such overlap to Candida pathogenesis.

SUMMARY OF THE INVENTION

With the emergence of drug-resistant Candida strains and a growing population of immunocompromised individuals, there is an mounting need to find new treatments for candidiasis.

In light of this need and others, the present invention has provided, in one aspect, a method for screening a therapeutic agent, comprising subjecting a first Candida culture to the agent and then determining the impact thereof on expression of a gene in the TUP1 pathway, such as SAP3, OP4 and TUP1 itself, whereby decreased expression of the gene is predictive of efficacy for said agent against candidiasis. In a preferred embodiment, the aforementioned determination comprises gauging expression of the gene by reference to the level of Tup1 protein or TUP1 transcript in the first culture.

DETAILED DESCRIPTION OF THE PREFERRED EMBODIMENTS

Figure 1:
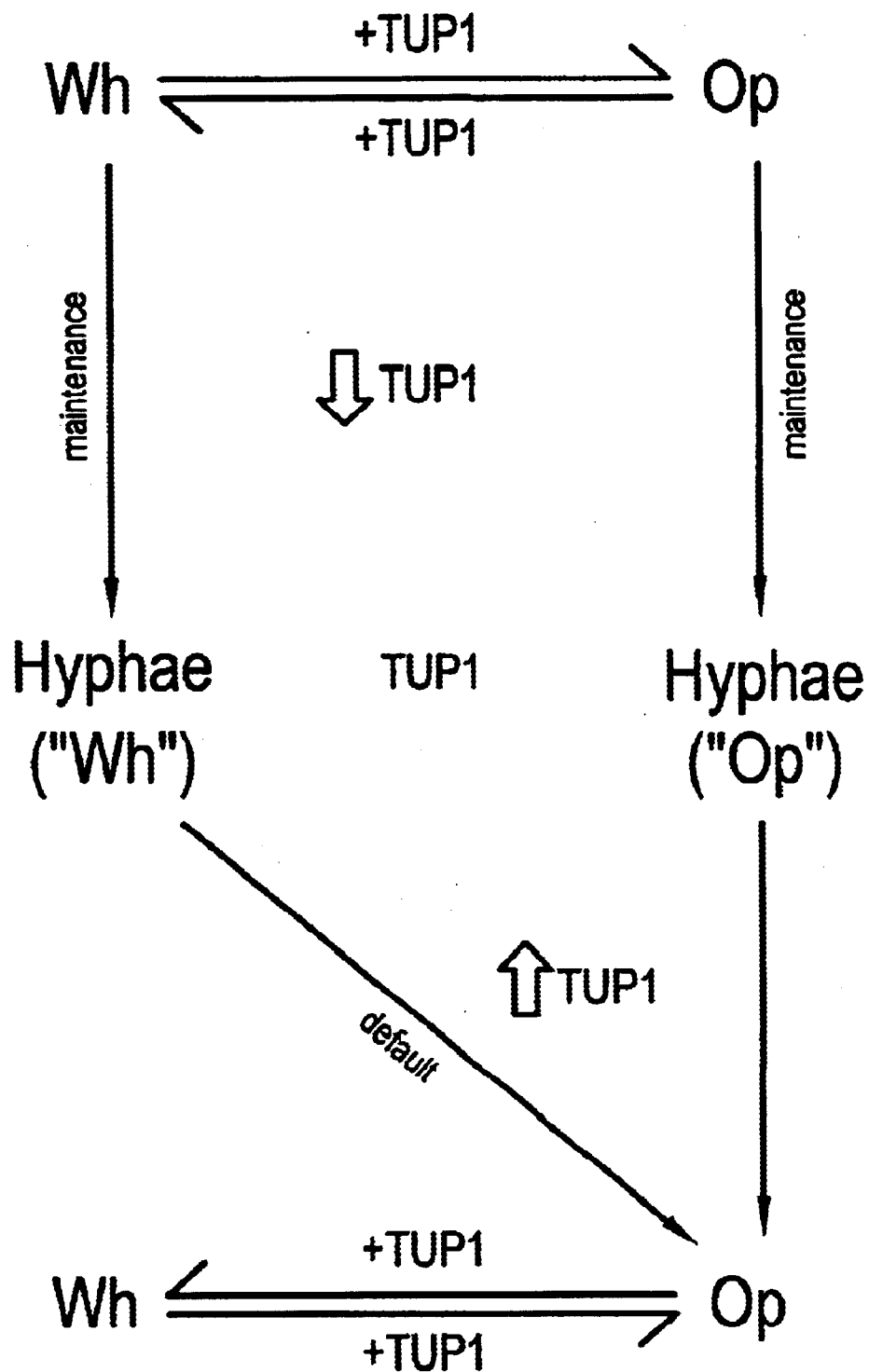
FIG. 1 is a schematic summary of experimental results that implicate a central role for TUP1 in the regulation of phenotype switching in Candida. When the TUP1 gene of *Candida albicans* is expressed at normal levels, phenotypic switching between white (Wh) and opaque (Op) phenotypes proceeds normally (top of drawing). Expression of TUP1 can be down-regulated (↑TUP1), by reducing the expression of a TUP1 gene, placed under the control of an inducible/repressible promoter and added to a TUP1 knockout (−TUP) strain. When TUP1 is thus down-regulated, cells from both the white phase and the opaque phase revert to hyphal phase growth. There is no phenotypic switching but the hyphal cells, to this point, maintain a memory of their original phase, as monitored by gene expression. When TUP1 expression is re-induced (↓TUP1), both white phase cells and opaque phase cells go from hyphal cells to opaque phase cells, but from opaque they can resume switching back and forth between white and opaque (bottom of drawing). Thus, TUP1 is essential for switching as well as setting the system at the "default" opaque phase.

The present inventors have discovered that TUP1, a gene previously identified in the context of controlling filamentous growth in *C. albicans*, plays a central role in the regulation of phenotype switching. This insight opens the way for screening compounds and therapeutic protocols for the ability to disrupt the pathway, controlled by TUP1, that is comprised of genes the expression of which affect switching specifically ("the TUP1 pathway").

Several transcriptional regulators function in the control of filamentous growth, including the respective expression products of the TUP1, CPH1 and EFG1 genes. Braun et al. (2000a). TUP1 encodes a protein, Tup1, that forms a transcriptional repression complex with another protein, Ssn6, that negatively controls a broad array of genes, Jabet et al. (2000), a significant fraction of which are induced during filamentous growth. Braun et al. (2000b). Among the genes identified as repressed by TUP1, however, only one (HWP1) also is known to be regulated by switching, regarding which TUP1 itself was not implicated heretofore.

As shown in FIG. 1, the inventors have found that, when TUP1 is knocked out in *C. albicans* strain WO-1, in which switching is dominated by a phase transition between white (Wh) and opaque (Op) colony-forming phenotypes, the yeast cells lose their ability to undergo the Wh/Op transition.

When the cells change from budding cells to hyphae and then back again to budding cells, moreover, they fail to maintain their original cellular phenotype; in other words, they lose "memory" of their previous phenotype. This memory is essential for maintaining phenotypic diversity.

Because the relevant phenotypes are observed readily, on a petri dish or in broth, one can screen for TUP1 knockout strains by cellular phenotype alone. By the same token, one can screen for inhibition of TUP1 function on the basis of cellular phenotype, in accordance with the present invention, and thereby identify compounds or protocols ("therapeutic agents") that impede or preclude phenotypic switching. The therapeutic agents thus identified would be candidates for use in treating or preventing Candida infections, by depriving the yeast of some or all of its phenotypic diversity and, hence, its ability to evade the immune system of a host.

Pursuant to one embodiment of the present invention, therefore, a plurality of Candida cells ("a Candida culture"), preferably *C. albicans* cells, is subjected to a therapeutic agent, under conditions that otherwise favor budding growth, and then is observed for a change to hyphal growth. The conditions favorable to budding growth include: a temperature in the range of about 30° C. to about 37° C.; and minimal media as defined by Bedell and Soll (1979).

A therapeutic agent that caused the dimorphic transition, budding-favorable conditions notwithstanding, thus would be identified as a prospect for inhibitor of TUP1 function, although further screening would be warranted to eliminate effects not specific to TUP1. According to one embodiment of the present invention, following the dimorphic switch to hyphal cells, the hyphal cells can be grown again, but in the absence of the putative agent, to monitor for the "reset" switch of all budding cells to the opaque phase, an indication of TUP1 up-regulation.

In accordance with another embodiment, therapeutic agents can be tested for an effect on TUP1-pathway genes, the expression of which are determined to be specific to the opaque phase. Two genes in the TUP1 pathway, OP4 and SAP3, presently are known to be opaque phase-specific in expression, but the present invention contemplates the use of other such genes that may be discovered in the future, for example, using a microarray system as described below.

For screening according to the present invention, effects on gene expression in the TUP1 pathway can be measured by any of several methodologies. These include but are not limited to measuring, in the cells of a Candida culture, (A) levels of Tup1 protein and/or TUP1 transcript (mRNA) or (B) the level of transcription of a reporter gene that is operably linked to the endogenous TUP1 promoter.

In relation to approach A, the level of Tup1 protein can be measured by performing two-dimensional gel electrophoresis, using the techniques of isoelectric-focusing and SDS-polyacrylamide gel electrophoresis, and autoradiography on the resultant gel. Comprehensive laboratory techniques regarding two-dimensional gel electrophoresis and autoradiography are detailed, for example, by Ausubel et al. (eds.), Current Protocols in Molecular Biology, Greene Publ. and Wiley-Interscience (New York, 1995) (hereafter "Ausubel et al. (1995)"), at Chapter 10 and Appendix 3.

Messenger RNA levels can be evaluated via northern blot, primer extension, and/or ribonuclease protection. Northern blotting entails a fractioning of total mRNA, via gel electrophoresis, a transferring of the mRNA fragments from the gel onto a filter, and a hybridizing of the target MRNA molecules with a labeled DNA or RNA probe. The primer extension procedure involved hybridizing an oligonucleotide primer to the 5' end of the target mRNA and extending the primer, using reverse transcriptase and unlabeled deoxynucleotides, to form a single-stranded DNA that is complementary to the template RNA. The resultant DNA then can be analyzed on a sequencing gel. The yield of the primer extension product quantifies the amount of mRNA produced by the cell. The ribonuclease protection assay measures mRNA levels by hybridizing sequence-specific RNA probes to sample RNAs. The probe anneals to homologous sequences in the sample RNA, and the presence of target RNA is analyzed and quantified by gel electrophoresis. See Ausubel et al. (1995), Chapter 4.

Alternatively, mRNA levels can be gauged, in implementing the present invention, by means of a miniaturized, gridded collection or "microarray" of short nucleotide chains (oligonucleotides), produced by means of a high-density, spatially directed synthesis technique described, for example, by Lipshutz et al. (1999). To this end, the oligonucleotides would be designed to hybridize, under conditions of appropriate stringency, to the mRNA transcript of a TUP1-pathway gene of interest. Thus, such a microarray would be contacted with a sample comprised of mRNA from a Candida culture employed in screening, according to the present invention, and the resultant hybridization, proportional to the expression level of the TUP1-pathway gene, would be quantified as detailed, for instance, in U.S. Pat. No. 6,040,138.

Pursuant to approach B, cells of a Candida culture are transformed with a reporter gene that is placed under the control of ("operably linked to") the promoter of TUP1 or another gene in the TUP1 pathway, such as SAP3 or OP4. Transcription of the reporter gene is monitored, after contact between the transformed cells and a therapeutic agent. For example, the promoter region of an endogenous TUP1-pathway gene can be operably linked to a luciferase gene, whereby expression of the former gene is reflected in the luciferase activity, which can be measured quantitatively, with a luminometer, as a bioluminescent reaction. Loss of luciferase activity would be monitored in the fashion described, for example, by Srikantha et al. (1996).

The present invention is further described by reference to the following example, which is illustrative only.

EXAMPLE 1

The TUP1 Pathway and the Wh/Op Switching System of *C. albicans*

The inventors determined that knocking out the TUP1 gene in *C. albicans* resulted not only in growth almost exclusively in hyphal phase but also a "turning off" of phenotypic switching (see FIG. 1). These effects were demonstrated by plating TUP1-deletion (−TUP1) strains at low density and then exposing them to UV light. Switching should have been enhanced under these conditions, but none was detected. In other words, there were no reversible changes in colony morphology of the hyphal colonies, and there was no white-opaque transition.

Further, an inserted copy of the TUP1 gene was placed under the control of the MET3 promoter in a −TUP1 strain. (As detailed by Care et al. (1999), the MET3 promoter is turned off in the presence of methionine and cysteine, and turned on in the absence of methionine and cysteine.) The promoter was inactivated in white cells and in opaque cells, respectively. Both cell types reverted to hyphae upon inactivation of TUP1, but they could be differentiated by their pattern of gene expression. When TUP1 was induced, the cells that started as opaque phase went back to opaque phase, but the cells that started out as white phase also went to opaque phase. Thus, the switching system was "reset" at a "default," which is the opaque phase, and TUP1 is necessary for setting the system.

Accordingly, TUP1 is necessary for switching. Further, the presence of TUP1 allows cells to maintain the white-opaque transition, as shown in FIG. 1.

CITED PUBLICATIONS

Balan et al. (1997) *J. Bacteriol.* 179:7210.
Bedell and Soll (1979) *Infect. Immun.* 26:348.
Braun et al. (2000a) *Genetics* 155:57.
Braun et al. (2000b) *Genetics* 156:31.
Care et al. (1999) *Mol. Microbiol.* 34:792.
Colombo et al. (1999) *Diagn. Microbiol. Infect. Dis.* 34:281.
Hellstein et al. (1993) *J. Clin. Microbiol.* 31:3190.
Hube et al. (1994) *Mol. Microbiol.* 14:87.
Jabet et al. (2000) *J. Biol. Chem.* 275:9011.
Kvaal et al. (1999) *Infect. Immun.* 67:6652.
Lipshutz et al. (1999) *Nature Genetics* 21 (suppl.):20.
Morrow et al. (1992) *Mol. Cell. Biol.* 12:2997.
Morrow et al. (1993) *Infect. Immun.* 61:1823.
Odds (1997) *Mycoses* 40 (Suppl. 2):9.
Pacheco-Rios et al. (1997) *Arch. Med. Res.* 28:229.
Pfaller (1996) *Clin. Infect. Dis.* 22 (Suppl. 2):S89.
Soll et al. (1987) *J. Clin. Microbiol.* 25:1611.
Soll et al. (1988) *J. Clin. Microbiol.* 26:1448.
Soll (1992) *Clin. Microbiol. Rev.* 5:183.
Soll (1996) *ASM News* 62:415.
Srikantha et al., (1996) *J. Bacteriol.* 178:121.

What is claimed is:

1. A method for screening a therapeutic agent, comprising subjecting a first Candida culture to said agent and then determining the impact thereof on expression of a gene in the TUP1 pathway, whereby decreased expression of said gene is predictive of efficacy for said agent against candidiasis and wherein said determining comprises observing whether said agent inhibits Wh-to-Op phenotypic switch, by cells of said first culture, under conditions favorable to said switch.

2. A method according to claim 1, further comprising a screening of said agent for an ability to inhibit a budding cells-to-hyphae transition, by cells of a second Candida culture, under conditions otherwise favorable to said transition.

* * * * *